(12) United States Patent
Hillman

(10) Patent No.: US 7,428,323 B2
(45) Date of Patent: Sep. 23, 2008

(54) METHOD AND SYSTEM FOR AUTOMATIC DIAGNOSIS OF POSSIBLE BRAIN DISEASE

(76) Inventor: Yitzchak Hillman, 10a Herzl Blvd., Jerusalem 96105 (IL)

( * ) Notice: Subject to any disclaimer, the term of this patent is extended or adjusted under 35 U.S.C. 154(b) by 0 days.

(21) Appl. No.: 11/334,365

(22) Filed: Jan. 19, 2006

(65) Prior Publication Data

US 2006/0120584 A1 Jun. 8, 2006

Related U.S. Application Data

(63) Continuation-in-part of application No. 10/437,448, filed on May 14, 2003, now abandoned, which is a continuation-in-part of application No. PCT/IL01/01047, filed on Nov. 14, 2001.

(30) Foreign Application Priority Data

Nov. 14, 2000 (IL) .................................... 139655

(51) Int. Cl.
*G06K 9/00* (2006.01)

(52) U.S. Cl. ..................... 382/128; 128/922; 128/923; 382/224; 600/410

(58) Field of Classification Search ................ 382/128, 382/130, 133, 224; 600/409, 410, 437; 128/922, 128/923

See application file for complete search history.

(56) References Cited

U.S. PATENT DOCUMENTS

| | | | | |
|---|---|---|---|---|
| 5,247,936 A * | 9/1993 | Hagiwara | ................... | 600/410 |
| 5,842,990 A * | 12/1998 | Kraske | ................... | 600/437 |
| 6,385,479 B1 * | 5/2002 | Sibbitt et al. | ................... | 600/410 |
| 6,400,978 B1 * | 6/2002 | Teicher et al. | ................... | 600/410 |
| 6,430,430 B1 * | 8/2002 | Gosche | ................... | 600/410 |
| 6,463,315 B1 * | 10/2002 | Klingberg et al. | ................... | 600/410 |
| 6,490,472 B1 * | 12/2002 | Li et al. | ................... | 600/410 |
| 6,697,660 B1 * | 2/2004 | Robinson | ................... | 600/409 |
| 6,785,409 B1 * | 8/2004 | Suri | ................... | 382/128 |
| 6,895,107 B2 * | 5/2005 | Park et al. | ................... | 382/133 |
| 7,037,267 B1 * | 5/2006 | Lipson et al. | ................... | 600/454 |
| 2003/0044055 A1 * | 3/2003 | Park et al. | ................... | 382/130 |
| 2004/0013291 A1 * | 1/2004 | Hillman | ................... | 382/128 |
| 2005/0197560 A1 * | 9/2005 | Rao et al. | ................... | 600/410 |
| 2005/0197561 A1 * | 9/2005 | Elsinger et al. | ................... | 600/410 |
| 2005/0273007 A1 * | 12/2005 | Burbar | ................... | 600/436 |
| 2006/0084858 A1 * | 4/2006 | Marks | ................... | 600/407 |
| 2006/0093583 A1 * | 5/2006 | Hartlep et al. | ................... | 424/93.2 |
| 2006/0120584 A1 * | 6/2006 | Hillman | ................... | 382/128 |
| 2006/0121036 A1 * | 6/2006 | Hartlep et al. | ................... | 424/145.1 |
| 2007/0100216 A1 * | 5/2007 | Radcliffe et al. | ................... | 600/300 |
| 2007/0191704 A1 * | 8/2007 | DeCharms | ................... | 600/411 |

FOREIGN PATENT DOCUMENTS

JP 05293173 A * 11/1993

* cited by examiner

*Primary Examiner*—Gegory M Desire

(57) ABSTRACT

A method and system for automatic diagnosis of possible brain disease is based on at least one brain scan image of a patient containing at least one feature of interest and a corresponding result of a medical profile analysis of the patient. A database containing parameters associated with at least one feature of a plurality of brain scan images each compiled from respective patient data and inserted into the database is searched so as to extract from the database a set of respective parameters each associated with the at least one feature and wherein in respect of each feature at least one of the corresponding parameters is indicative of a brain disease profile. The set of respective parameters is analyzed to determine a statistically significant brain disease profile which fits the patient based on the at least one feature of interest of the patient's brain scan image.

26 Claims, No Drawings

METHOD AND SYSTEM FOR AUTOMATIC DIAGNOSIS OF POSSIBLE BRAIN DISEASE

RELATED APPLICATIONS

This application is a continuation-in-part of U.S. application Ser. No. 10/437,448 filed May 14, 2003 now abandoned and entitled "A METHOD AND A SYSTEM FOR COMBINING AUTOMATED MEDICAL AND PSYCHIATRIC PROFILING FROM COMBINED INPUT IMAGES OF BRAIN SCANS WITH OBSERVED EXPERT AMD AUTOMATED INTERPRETER USING A NEURAL NETWORK," which is a continuation-in-part of International application No. PCT/IL01/01047, filed Nov. 14, 2001, which claims the benefit of Israeli application No. 139655, filed Nov. 14, 2000. All related applications listed above are incorporated herein by reference in their entireties.

FIELD OF THE INVENTION

The present invention generally relates to a field of image processing and data image classification. More particularly, the present invention relates to a system and a method for detecting, processing and classifying biometric images using digital images.

BACKGROUND OF THE INVENTION

This invention relates to use of a computer based technique to predict brain disease, brain degenerative disease and atrophy as well as other psychiatric illnesses before their onset. The brains of people with Alzheimer show early atrophy before onset of diseased symptoms. Schizophrenia patients show minor changes even before their first psychotic episode. That raises the possibility of screening and early diagnosis for the disease and early intervention for people at risk.

This invention is an automated tool comprising a computed algorithm for the sake of providing automated early diagnosis of disease and psychiatric conditions.

There are many tools and procedures for obtaining brain scan images. Likewise, there are countless algorithms and methods intended to improve scan images using image processing and feature extraction and classifier/discriminant function techniques. Among these are those described in the following publications (not all of which are valid prior art) whose contents are incorporated herein by reference:

"*Fuzzy region integration approach for subcortical structure segmentation*" by Shichun Peng et al. Proceedings of the 9th International Conference on Neural Information Processing (ICONIP'OZ), Vol. 3;

"*Automated Characterization and Recognition of 2D and 3D Brain Structure in MRI for Diagnostic Support*" by Rasmus Larsen, Lars Hanson & Karl Skoglund et al. Apr. 10, 2003 shown in a PhD Project Poster presentation at the Technical University of Denmark (Informatics and Mathematical Modeling)

"*Pattern of cerebral hypoperfusion in Alzheimer disease and mild cognitive impairment measured with arterial spin-labeling MR imaging*" by Johnson NA et al. Radiology 2005 March; 234 (3): 851-9;

"*Discrimination between Alzheimer dementia and controls by automated analysis of multicentre FDG PET*" Neuroimage 2002 September: 17 (1) 302-16.

There are numerous U.S. patents on segmentation and image processing of human tissue including for example U.S. Pat. Nos.: 4,991,092; 5,812,691; 6,718,055; 4,922,915; 4,736,751; 6,952,097; 6,574,566; 4,991,092; and 5,873,823.

Two relevant publications published well after the priority date of the present application are U.S. Patent Application No. 2003/0228042 entitled "*Method and system for preparation of customized imaging atlas and registration with patient image*", and a corresponding research paper entitled: "*Image Study Summarization of MR Brain Images by Automated Localization of Relevant Structures*", by USHA SINHA et al., Ann. N.Y. Acad. Sci. 980: 278-286 (2002). The research paper deals with object segmentation and localization having a final goal as defined by its authors ". . . to identify relevant slices of an imaging study that has several important applications in image integration with the electronic medical record, in automated creation of teaching files, and in clinical compression." The paper discusses a methodology to objectify the patient presenting condition by automated selection of relevant images from a serial MR study. Structured data entry is used to capture the patient's chief complaint, pertinent history, signs, and symptoms. Expert created rules use this data to arrive at a differential and to identify the affected brain region/structure. Another expert created knowledge base then maps this information to the relevant image type, including image sequence specifics and orientation. A DICOM study reader identifies the relevant imaging sequences from the MR study. The structure localization method involves a search based on principal component analysis. A training set of subimages containing the structure of interest is used to generate a basis set of prototype images called eigenimages. The structure is located in an image by searching the image for a subregion that best matches the basis set. The structure localization was used to locate the lateral ventricles and orbits in nine images that were not part of the training set. The automated localizations were compared to expert localizations and the center of the regions located by the two techniques agreed to within ±1.7 mm. (average for the nine localizations each of two structures).

The contents of all the above-mentioned research papers, patents and patent applications are incorporated herein by reference.

Efficient automated diagnostic tools for brain scan images have one thing in common. They must all contain within their algorithms a method of data classification and storage as well as a method for training the classifier using an expert interpreter.

Early treatment with behavioral therapy or drugs could prevent, or at least mitigate, the full onset of Alzheimer or even schizophrenia. The longer the disease or psychosis goes untreated, the worse the outcome. Alzheimer and Schizophrenia is probably the most expensive diseases for the National Health Service of any country. If it can be prevented by early detection, the implications are vast.

Magnetic resonance imaging (MRI) in brain scans showed significant differences between healthy brains versus those of patients. The brain changes began some time before the Alzheimer or schizophrenic patients first suffered dementia or a psychotic episode.

Over the clinical course of Alzheimer, patients demonstrate progressive declines in functional ability that correlate with MMSE scores. In the preclinical phase, also called MCI, patients with MMSE score greater than 23 will demonstrate minimal impairment—generally, mild memory loss—while functioning normally and independently.

Atrophy rates for brain temporal lobe, cortex, Amygdalae, temporal gyrus, hippocampus, and entorhinal cortices are significantly increased in patients compared with controls. Linear extrapolation backward suggested medial temporal lobe atrophy commenced 3.5 years before onset of symptoms, when all patients were asymptomatic. Medial temporal lobe atrophy rates are an early and distinguishing feature of Alzheimer. Atrophy rates for brain, temporal lobe, hippocampus, and entorhinal cortices are significantly increased in patients compared with controls.

Schizophrenia patients have significant deficits in cortical gray matter and in temporal lobe gray matter. The temporal lobes of the brain are linked with speech and the experience of hallucinations. There were also significant differences in whole brain volume, as well as significant enlargement of the lateral and third ventricles. Structural deviations were found in both untreated and minimally treated subjects. No relationships were found between any brain matter volumes and positive or negative symptoms. Structural brain abnormalities were distributed throughout the cortex with particular decrement evident in gray matter. This feature is consistent with altered cell structure and disturbed neuronal connectivity, which accounts for the functional abnormality of psychosis. These brain abnormalities were not specific to schizophrenia; they were also present in the brains of people suffering from other kinds of psychosis, such as bipolar disorder. It is assumed that many mental illnesses begin with the same changes in brain structure and chemistry and that an initial common pathway diverges into different forms of mental illness. This means that treating anyone showing signs of the brain abnormalities should prevent the onset of other mental diseases as well.

The process of decoding and analyzing brain scan images so as to provide an accurate psychiatric profile of individuals is difficult if not virtually impossible to provide under human evaluation.

U.S. Pat. No. 5,632,276 (Eidelberg et al.) discloses a method and apparatus for screening patients for nervous system dysfunction including neurological capacity and dysfunction. A patient profile of actual functional activity of a brain of a patient is produced and compared with at least one marker. The marker is a profile of predetermined functional activity at a plurality of sets of predetermined coordinates of a given brain geometry. It appears that the database search and comparison are performed in respect of different data associated with a single patient.

U.S. Pat. Nos. 6,205,236, 5,999,639 and 6,115,488 to Rogers et al. disclose a method and system for detecting and displaying clustered microcalcifications in a digital mammogram, wherein a single digital mammogram is first automatically cropped to a breast area sub-image which is then processed by means of an optimized difference of Gaussians filter to enhance the appearance of potential microcalcifications in the sub-image. The potential microcalcifications are thresholded, clusters are detected, features are computed for the detected clusters, and the clusters are classified as either suspicious or not suspicious by means of a neural network. Thresholding is preferably by sloping local thresholding, but may also be performed by global and dual-local thresholding. The locations in the original digital mammogram of the suspicious detected clustered microcalcifications are indicated. Parameters for use in the detection and thresholding portions of the system are computer-optimized by means of a genetic algorithm. The results of the system are optimally combined with a radiologist's observation of the original mammogram by combining the observations with the results, after the radiologist has first accepted or rejected individual detections reported by the system.

Reference is also made to "*Alzheimer's disease and models of computation: Imaging, classification, and neural models*" by Hojjat Adeli et al. appearing in Journal of Alzheimer's Disease 7 (2005) 187-199. Although this article is not prior art to the present application, which derives from PCT/IL01/01047 filed Nov. 12, 2001 and claiming Priority from IL 139655 filed Nov. 14, 2000, it is nevertheless interesting for its conclusion which appears to corroborate the earlier researches of the present inventor. Thus, particular reference is made to the conclusion which notes that researchers have not yet found conclusive evidence regarding the specificity and sensitivity of the neurological markers and diagnostic techniques based on them for the diagnosis of Alzheimer's disease. Similarly, there seems to be no consensus regarding the various hypotheses of progression of AD from the point of view of different disease states (such as MCI, PDAT, and SDAT) and clear cut boundaries between them. It was concluded that a combination of parameters from different investigation modalities seems to be the way to go for increasing the accuracy of detection and diagnosis.

In a research paper entitled "*MRI and CSF studies in the early diagnosis of Alzheimer's Disease*" by M. J. de Leon et al. appearing in Journal of Internal Medicine 2004; 256: 205-223 it is noted that the combined use of MRI and cerebrospinal fluid diagnostic measures for Alzheimer's Disease has the promise to improve the early and specific diagnosis of Alzheimer's Disease.

There is no suggestion in the scientific or patent literature preceding the priority date of the present application to facilitate the diagnosis of brain disease in general, and Alzheimer's Disease in particular, by searching a database containing parameters associated with at least one feature of a plurality of brain scan images each compiled from respective patient data and inserted into the database so as to extract from the database a set of respective parameters each associated with a feature of interest and wherein in respect of each feature at least one of the corresponding parameters is indicative of a brain disease profile; and analyzing the respective parameters to determine a statistically significant brain disease profile which fits a patient based on the at least one feature of interest of a brain scan image of the patient.

Therefore, it would be desirable to provide a method and system to diagnose and profile brain disease such as dementia (especially Alzheimer) and psychiatric illness using a database of brain scan images and associated parameters.

SUMMARY OF THE INVENTION

It is an object of the invention to provide a method and system for automatic diagnosis of possible brain disease.

A particular object of the invention is to profile dementia (especially Alzheimer) and psychiatric illness using images of brain scans.

These objects are achieved in accordance with a first aspect of the invention by a method for automatic diagnosis of possible brain disease, said method comprising:

obtaining at least one brain scan image of a patient containing at least one feature of interest and a corresponding result of a medical profile analysis of the patient;

searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile; and analyzing said set of respective parameters to determine a statistically significant brain disease profile which fits said patient based on the at least one feature of interest of the patient's brain scan image.

In accordance with a second aspect of the invention there is provided a system for automatic diagnosis of possible brain disease, said system comprising:

a data extraction unit for searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile; and an analysis unit coupled to the data extraction unit for analyzing said set of respective parameters to determine a statistically significant brain disease profile which fits said patient based on at least one feature of interest of a brain scan image of the patient.

Using MRI or other tools with brain scan analysis, the present invention uses the creation of a neural network or a multi-layer perceptron (MLP) neural network (NN) in which a centralized data bank combines brain scan images with experience from expert psychiatric advice and diagnosis placing emphasis on medical and psychiatric history of individuals being analyzed. The computer algorithms involved in this procedure have already proved themselves clinically in other applications such as that described in U.S. Pat. Nos. 6,205,236, 5,999,639 and 6,115,488 to Rogers et al. where very similar Neural Network based algorithms are currently used.

Evolutionary development of the human brain occurred at the same time as the palms and during the first tool creation era of the first humans. Human brain and palm morphologies resultantly bear correlations. Another objective of the present invention is to complement the above-mentioned method of diagnosis and profiling while emphasizing the measurements of hardness of specific mounts and areas of the skin, the bending angle of the fingers, spacing between the fingers, relative finger lengths, the mounts on fingers, finger formations on closed or clapped hands as well as other features of the palms. This provides for more accurate psychiatric profiling allowing correlations to be found between palm, hand and foot features, and features on brain scans. This may provide insight into psychiatric, psychological and character profiling. This is important in brain research as well as in providing more accurate diagnostics.

Another objective of the present invention is the classification of brain scans using MRS and fMRI (Magnetic Resonance Spectroscopy and Functional MRI) indicating brain morphology or functional characteristics of the brain (i.e. neural activity).

It is assumed that different classifications of character, personality, psychological and psychiatric profiles have a different spread of neural activity for similar neural stimuli, such as specific sight, sound, vocal, smell, touch, taste, suggested imagination or other. The invention is directed, in one of its embodiments, to find and use unique specific neural activity associated with each of these specified classifications indicating the link between the neural activity and the classification. Finding such a link and classifying it in the form of a computed neural network will aid in the psychiatric diagnosis, making it more accurate.

Using brain scan technology, we are now able to identify the content of a person's thought, albeit in a very limited context. However, it is assumed that although, the basic pattern of neural firing is maintained in the general population, significant variations on the general pattern apply. These variations are dependent on factors that include the psychiatric profile of the person.

Previous studies have shown that brain areas can be selective for processing a particular type of visual information. In the cortical brain regions associated with mental processing, the fusiform face area responds strongly to faces while the para-hippocampus place area responds strongly to indoor and outdoor scenes depicting the layout of local space. It has also been found that the magnitude of activity in these two brain areas is much livelier or stronger when one is seeing the picture (physically present in front of them) compared with just imagining it.

Portable scanning techniques (such as laser scanners) can be used to gain some insight into what is happening in the minds of people who are unable to communicate because they are suffering from an injury or disorder that makes speech impossible. However, it is assumed that it will be possible to predict and analyze thought patterns with almost 100% accuracy if adjustment is made for the thought pattern analysis by taking into consideration the psychiatric profile of the individual being analyzed. Therefore, another objective of this patent is to categorize neural functional activity (agitated by specified stimuli) according to the psychiatric profile thereby providing for a method and system for analyzing thoughts. This procedure has special emphasis for the need of prostheses limbs in order to function.

A computed neural network is used to correlate sequenced brain neural activity with memorized sequences of template scan images recorded in a central database of template scan images that have been classified according to their psychiatric profile.

Other objectives and advantages of the invention will be apparent from the following detailed description that follows.

In the present invention, the terms "psychiatric profiling" or "diagnosis" are intended to include profiling such as medical, psychiatric, genetic, psychological and character profiling.

In a specific form the present invention provides a method for providing human psychiatric profiling using a process of analysis and classification of brain scan images comprising; a) obtaining a 3-D brain scan image and the result of a psychiatric profile analysis and parameters used to enhance the image of the scan; b) extracting the edges of the brain scan image, pinpointing reference points on it, positioning, standardizing its size, and aligning it; c) autocropping and extracting a specified plurality of features and regions and/or parameters within the brain scan; d) voting, matching or correlating extracted regions, images and parameters of a plurality of features of the scan with database template images and parameters; e) searching in a message memory for a plurality of messages that make up the profile of an individual, wherein each message corresponds to the respective feature or combination of features of a database, outputting each one of the said plurality of messages concurrently to form a first profile set of messages; f) obtaining a second set of feature detections and related message statements; g) accepting some output detections and related messages in the first set to form a third profile set of features and related messages that is a subset of the first set, combining the third profile set of messages with the second set to form a fourth set, alternatively allowing the fourth set to equal the first set, alternatively allowing the third set to equal the second set; h) storing in the said message memory the fourth set of detections and related messages corresponding to the said brain scan image or storing in the said message memory the fourth set of detections and related messages corresponding to a new combination of features on the brain scan image, providing a corrected output based on said corrected fourth set of detections and related messages.

According to one preferred embodiment of the method, the said features of the brain scan is one or a combination of general anatomic structures including CSF, gray matter, ventricular fluid, and lesioned tissue white matter, neurological mapping of activity to specified stimuli (such as specific sight, sound, vocal, smell, touch, taste, suggested imagination or other).

According to a preferred embodiment of the method, the said second set is composed of none, one or a combination of the elements of the set of feature detections and related message statements that form a human profile made by an expert interpreter.

In one embodiment, said second set is composed of none, one or a combination of the elements of the set of feature detections and related message statements that form a self profile of a person under analysis. In such case, in one embodiment the detections and related messages accepted from the first output set are selected according to their likelihood of correct output detection reporting and analysis.

The invention proposes the use of a neural network and as such includes a fuzzy logic type of classifier. Other classifiers included can be used instead or in a combination of computational paradigms such as wavelet transforms, chaos theory, simple parametric statistical tests (such as t-test and analysis of variance), k-means cluster and k nearest neighbor analysis (see: J. Benvenuto, Y. Jin, M. Casale, G. Lynch and R. Granger, "*Identification of diagnostic evoked response potential segments in Alzheimer's disease*", Experimental Neurology 176 (2002), 269-276)., "*Classifier based on linear discriminant analysis (LDA)*"—(see: R. Higdon, N. L. Foster, R. A. Koeppe, C. S. DeCarli, W. J.) Jagust, C. M. Clark, N. R. Barbas, S. E. Arnold, R. S. Turner, J. L. Heidebrink and S. Minoshima, "*A comparison of classification methods for differentiating frontotemporal dementia from Alzheimer's disease using FDG-PET imaging*", Statistics in Medicine 23 (2004), 315-326).

Using a mixture of markers and a combination of computational techniques can increase the accuracy of algorithms for automated detection and diagnosis of Alzheimer Disease and differentiating in from other dementia.

Brain scan images are provided via an Internet or GRID network connection and are analyzed by the procedures described. In this manner, the centralized database can be globally accessed.

Though sensitivity issues are less of a problem in diagnosing dementia per se, specificity issues differentiating Alzheimer from ordinary age related dementia proves a main hurdle. MRI perfusion scan image with additional MRI structural imagery proves to be an effective base image system to diagnose early stages of Alzheimer using the Neural Network Computed method described. Both Voxel-Based Morphometry and volumetric changes, structural and functional variations are recorded on the database for analysis using the neural network classifier. The advantages of using a Neural network/Fuzzy logic type of analysis is that structural atrophy can be classified not only by volumetric single or small parameter system but by a multi parameter classifier of normalized images having a multitude of variation of 3-D shapes in a time dependent (age or durational progression of the disease) axis. The spatial normalization step aims to map each structural MRI to a template in standard 3-D and stereotactic space.

In another embodiment, the input image is from an MRI scanner, fMRI, MRS, PET, CAT, SPECT, EEG, laser, or other.

In another embodiment the input image is provided in a form of a computer memory of 2-D slices forming a 3-D map or alternatively of a complete 3-D image.

In another embodiment the pinpointing of reference points is done by use of a matching template images.

In another embodiment, known reference points are built into the input image.

In another embodiment areas and features are extracted using referencing to known given or calculated reference points.

In another embodiment the psychiatric analysis results are the profile results provided by readings of hand and foot palms.

In another embodiment a standardized normalized image is determined using a generic algorithm that uses the scanner image enhancement parameters as input parameters provided into the generic algorithm procedure.

In another embodiment, the edge extractor or the position registration circuit, or the feature extractor, comprises a neural network or in which the pinpointing of reference points on the brain scan is done after and as a result of the position registration using a neural network, or in which the voting, matching and correlating extracted regions and images of features with database template images is done using a neural network or in which the storing of the fourth set of detected features and related messages is in a form of a neural network or in which detection is performed by brain scan detector comprising a neural network.

In such case, in one embodiment the neural network is a multi layer peceptron neural network.

In another embodiment the pinpointing of reference points is done by setting the palm, hand or foot in an encompassing fixed shell before imaging thereby referencing from the outer shell.

In one embodiment the method is performed using a device for measuring hardness and softness of specific mounts and areas of the skin, the bending angle of the fingers and finger formations on closed or clapped hands in order to provide further input and image data to the already available brain scan images for the purpose of psychiatric and psychological diagnosis. An example of such data type is described in: "*Finger length ratio (2D:4D) correlates with physical aggression in men but not in women*" by Allison A. et al. in Biological Psychology 68 (2005) 215-222.

In such case, in one embodiment, a mechanically driven and controlled blunt pin element is used to press automatically on the skin and palm mounts. In another embodiment the pressure applied is controlled and measured, and rebound rate of the skin and palm mount is measured using a laser scanner.

In one embodiment auto-cropping and voting are performed by a generic algorithm in which auto-cropping and voting parameters are automatically optimized using a generic algorithm that maximizes fitness.

There is also provided in accordance with a specific embodiment of the present invention a system for providing human profiling using the method as defined in any of the preceding claims comprising of: a) a mechanically driven blunt-pointed element adjoining an apparatus for measuring the angle of finger bending; b) a mechanically driven plate used for measuring the maximum allowed bending angle of the finger adjoining the apparatus; c) RAM memory storage; d) an microprocessor; e) input drive; f) a high resolution color printer; g) a computer operating system.

DETAILED DESCRIPTION OF SOME EXEMPLARY EMBODIMENTS

A brain scan is provided using conventional brain scanning techniques.

Parameters used in obtaining the scan are provided. These parameters indicate either filtering, thresholding or other image enhancing parameters used in obtaining the scanned image. Brain scans of different "slices" and planes at differing given angles of the brain make up the input image to the system providing for a 3-D image of the brain. This scan is stored in memory. Ordinary MRI may map gray and white matter, ventricular fluid, and lesioned tissue using both or either T1 or T2 times. MRS fMRI and PET scans give other mappings.

In order to normalize and standardize the scans, into a standard scan image, a generic algorithm is used. Scan image normalization uses the input parameters provided with the original brain scan image as parameters used in this generic algorithm.

A feature extractor is used for finding reference points on the brain image.

Pinpointing reference points is done automatically by matching template images of the brain to database images of brains. A second feature extractor process or circuit is provided for extracting all the features necessary for profiling analysis of an individual. These include specific 2-D slices or plains on the 3-D brain scan image at specific brain areas and angles. Areas and features of these images are extracted by using a process of referencing from a given set of reference points on similar brain scan images.

A protocol for brain extraction and automatic tissue segmentation of MR images involves the brain extraction algorithm, proton density and T2-weighted images used to generate a brain mask encompassing the full intracranial cavity. Segmentation of brain tissues into gray matter (GM), white matter (WM), and cerebral spinal fluid (CSF) is accomplished on a T1-weighted image after applying the brain mask. The fully automatic segmentation algorithm is histogram-based and uses the Expectation Maximization algorithm to model a four-Gaussian mixture for both global and local histograms. The means of the local Gaussians for GM, WM, and CSF are used to set local thresholds for tissue classification. Reproducibility at the regional level by comparing segmentation results within the 12 major Talairach subdivisions.

A voting process or circuit compares the extracted brain scan features with a database of previously extracted brain scan features to categorize the object within a set of objects having similar or highly correlated images of the features by use of a neural network.

The results of the system are optimally combined with the results given by the neural network computation.

Additional measurements of palm hand or foot are made. In order to measure hardness and softness of the palms of hand and foot regions, specific regions on the hand and foot are pressed using a mechanically driven and controlled blunt pin element that is pressed automatically on the skin and palm mounts. The pressure applied is controlled and measured. Rebound rate of the skin and palm mount is measured using a laser scanner.

Similarly, in order to measure the maximum bending angles of the fingers, automated controlled and measured pressure is applied on the fingers using a mechanically driven plate while measuring the maximum allowable bending angle of the finger.

An edge extractor processes the brain scan images in order to determine the edges of the brain in the image. This is done simply by matching template images of objects having predetermined outer edges declared as belonging to the object features.

Auto-cropping is performed by one of many methods. Auto cropping of specific regions on the brain scan images is optimized by parameter-optimizing means using a generic algorithm (GA) so as to maximize the true-positive image detection rate while minimizing the false-positive detection rate. Of course, other optimization schemes may be used as well. Preferably, the cropping is performed automatically, although the images could be cropped manually, and the results stored as potential templates used for additional automatic classification.

Generic algorithms search the solution space to maximize a fitness (objective) function by use of simulated evolutionary operators. In the present invention, the fitness function to be maximized reflects the goals of maximizing the number of true-positive pixel elements of major lines while minimizing the number of false-positive detections. The use of generic algorithms requires determination of several issues: objective function design, parameter set representation, population initialization, choice of selection function, choice of genetic operators (reproduction mechanisms) for simulated evolution, and identification of termination criteria.

The design of the objective function is a key factor in the performance of any optimization algorithm. The function optimization problem for detecting brain scan image features may be described as follows: given some finite domain, D, a particular set of feature detection parameters, $x=\{t, f, k_{lo}, k_{hi}, \ldots, d\}$ where x is an element of D, and an objective function $f_{obj}$, where x denotes the set of real numbers, find the x in D that maximizes or minimizes $f_{ob}$. Optimization may be achieved by maximizing the true positive rate (TP) for a feature relating to a given profile assessment message subject to the constraint of minimizing the false positive (FP) rate. Assuming TN represents profile elements and features correctly identified as not belonging to the objects under investigation, and FP represents profile elements and features reported as belonging to the objects under investigation. TP is the set of profile elements and features reported by a CAD, and FN is set of profile elements and features that are known to be true and that are not reported by CAD.

Systems may be optimized to maximize the TP and additional FN rates subject to the constraint of minimizing the FP rate. Different objective functions may be used.

This embodiment also seeds the initial population with some members known beforehand to be in an interesting part of the search space so as to iteratively improve existing solutions. The number of members is limited to some pre-determined number greater or equal to 1 so as to reduce the computational cost of evaluating initial objective functions.

In one embodiment of the invention, normalized geometric ranking is used, as described in greater detail in "*A Generic algorithm for function Optimization*", by Houck, et al. in Tech. Rep., NCSU-IE 95-09, 1995, for the probabilistic selection process used to identify candidates for reproduction. Ranking is less prone to premature convergence caused by individuals who are far above average. The basic idea of ranking is to select solutions for the mating pool based on the relative fitness between solutions. This embodiment also uses the default genetic operation schemes of arithmetic crossover and non-uniform mutation included in the generic algorithm described by above-mentioned Houck et al.

This embodiment continues to search for solutions until the objective function converges. Alternatively, the search can be terminated after a predetermined number of generations. Although termination due to loss of population diversity and/ or lack of improvement is efficient when crossover is the primary source of variation in a population, homogeneous populations can be succeeded with better (higher) fitness when using mutation. Crossover refers to generating new members of a population by combining elements from several of the most fitting members. This corresponds to keeping solutions in the best part of the search space. Mutation refers to randomly altering elements from the most fitting members. This allows the algorithm to exit an area of the search space that may be just a local maximum. Since restarting populations that may have converged proves useful, several iterations of the generic algorithm are run until a consistent lack of increase in average fitness is recognized.

Once potentially optimum solutions are found by using the generic algorithm, the most fitting solution of the generic algorithm may be further optimized by local searches. An alternative embodiment of the invention uses the simplex method to further refine the optimized solution of the generic algorithm.

The auto-cropping system may also benefit from optimization of its parameters including contrast value, number of erodes, number of dilates and other parameters.

The method for optimizing the auto-cropper includes generating line masks by hand for some training data, selecting an initial population, and producing line masks for training data. The method further includes measuring the percent of overlap of the hand-generated and automatically generated masks as well as the fraction of auto-cropped features outside the hand-generated masks. The method further comprises selecting winning members, generating new members, and iterating in a like manner as described above until a predetermined objective function converges.

Thresholding, contrast and image enhancing parameters used by a particular brain scanner may be assumed as input parameters that are fed into system and associated with the particular brain scan image. These parameters are used for standardizing and normalizing the scanned image using generic algorithm techniques.

Feature extraction is obtained by first identifying and aligning the image brain scan using template matching then by use of further template matching, a point on the object being chosen as a reference point. Features are then extracted by template matching with reference to the different reference points such that the bigger the brain area size, the larger the area chosen for template matching. This brain size image adjustment is controlled by a parameter that is included amongst the optimization parameters optimized in the feature detection and auto cropping process.

Relevant features within objects are obtained according to the invention by providing a novel method and system for automated feature detection from digital object images. Parameters necessary for cropping the relevant digital feature images are optimized; the digital feature images are cropped based on the optimized cropping parameters for selecting profile and relevant feature for further analysis.

The detected features and relating profiles are then stored as a detection image and profile (constituting an initial dataset), the detection image and profile is processed for display, and a computer-aided detection image is produced for review by an expert such as a psychiatrist etc.

Based on an iterative approach, the expert helps to create an enhanced dataset containing at least partial data in the initial dataset for which the corresponding parameters have been determined empirically to provide a better match to the brain disease profile. The enhanced dataset may be formed by augmenting the initial dataset by a respective brain disease profile of a plurality of patients based on at least one additional feature of interest. Alternatively, the enhanced dataset may be formed by rejecting at least one feature of interest in the initial dataset that is found empirically not to be significant.

In accordance with one embodiment of the invention the enhanced dataset is formed as follows. The expert first reviews the initial dataset including the original scan image, reports a profile and a set of suspicious regions and features of interest that diagnose the particular profile and feature set, S1. S1 is a subset of all possible profiles and features S of the objects under investigation. A CAD (computer aided diagnosis) system, or more particularly the CAD system of the invention, operates on the original set of suspicious regions and features and reports a second set of suspicious diagnosis or regions of interest, which form profile and features set S2. The expert then re-examines the set S2, accepts, or rejects members of set S2, thus forming a third profile set S3 that is a subset of set S2. The expert then forms another set S4 that is a set of all profile attributes that belong to S1 in union with profile attributes S3. The workup regions in S4 and the patients under analysis having S4 are then recommended for further psychiatric examination and diagnosis.

CAD system outputs are thereby incorporated with the expert's analysis in a way that optimizes the overall sensitivity of detecting true positive features and regions of interest as well as associated profile assessments.

Likewise, the database may be updated with corresponding parameters associated with the at least one feature of interest of the patient's brain scan image. Thus, once it is established that a certain patient is suffering from a particular brain disease, the patient's record may be added to the database or the requisite parameter in the database may be updated for the patient, if his record already exists. By such means, the accuracy of the database is enhanced over time and the ability to diagnose brain disease based on historical data stored in the database is constantly improved.

The digital images are stored as digital representations of the original feature images on computer-readable storage media. In a preferred embodiment reduced to practice, the digital representations or images were stored on a 12 GB hard drive of a general-purpose computer such as a PC having dual Pentium III microprocessors running at 566 MHZ, 512 MB of RAM memory, a high resolution color monitor, a pointing device, and a high resolution color inkjet HP printer. The system operated within a Windows 2000 operating system connected via a modem to the Internet so as to receive and send results from around the globe via a worldwide network.

Template features are provided as inputs to the classifier, which classifies each template or combinations of templates as being associated with particular psychiatric or psychological set of profile elements or "statements".

In practice, a feature detector is only able to locate regions of interest in the digital representation of the original object that may be associated with a particular profile element or "statement". In any detector, there is a tradeoff between locating as many potentially suspicious regions as possible versus reducing the number of normal regions falsely detected as being potentially suspicious. CAD systems are designed to provide the largest feature detection rates possible at the expense of detecting potentially significant numbers of irrelevant regions. Many of these unwanted detections are removed from consideration by applying pattern recognition techniques.

Pattern recognition is the process of making decisions based on measurements. In this system, regions of interest or detections are located by a detector, and then accepted or rejected for display. The first step in the process is to characterize the detected regions. To this end, multiple measurements are computed from each of the detected regions. Each measurement is referred to as a feature. A collection of measurements for a detected region is referred to as a feature vector, wherein each element of the vector represents a feature value. The feature vector is input to a discriminant function. A classifier has a feature vector x applied to a set of discriminant functions g (x). A discriminant function computes a single value as a function of an input feature vector. Discriminant functions may be learned from training data and implemented in a variety of functional forms. The output of a discriminant function is referred to as a test statistic. Classification is selecting a class according to the discriminant function with the greatest output value. The test statistic is compared to a threshold value. For values of the test statistic above the threshold, the profile set associated with the feature vector is retained and displayed as potentially suspicious. When the test statistic is below the threshold, the profile set is not displayed.

Many methods are available for designing discriminant functions. One approach considered for this invention is a class of artificial neural networks. Artificial neural networks require training, whereby the discriminate function is formed with the assistance of labeled training data.

In a preferred embodiment, the classification process is implemented by means of a multi-layer perceptron (MLP) neural network (NN). It will be appreciated that other embodiments may use classifiers such as, for example, a statistical quadratic classifier, wavelet transforms, chaos theory, simple parametric statistical tests (such as t-test and analysis of variance), k-means cluster and k nearest neighbor analysis, or a classifier based on linear discriminant analysis. Using a mixture of markers and a combination of computational techniques can increase the accuracy of algorithms for automated detection and diagnosis of Alzheimer Disease and differentiating in from other dementia.

The embodiment of the MLP neural network system is implemented by means of software running on a general-purpose computer possibly containing parallel processors. Alternatively, the MLP neural network could also be implemented in a hardware configuration by means readily obtained apparent to those with ordinary skill in the art.

The weight values are obtained by training the network. Training consists of repeatedly presenting feature vectors of known class membership as inputs to the network. Weight values are adjusted with a back propagation algorithm to reduce the mean squared error between actual and desired network outputs. Desired outputs of $z_1$ and $z_2$ for a suspicious input are +1 and −1, respectively. Desired outputs of $z_1$ and $z_2$ for non-suspicious inputs are −1 and +1, respectively. Other error metrics and output values may also be used.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

The invention claimed is:

1. A method for automatic diagnosis of possible brain disease, said method comprising:
   obtaining at least one brain scan image of a patient containing at least one feature of interest and a corresponding result of a medical profile analysis of the patient;
   searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile;
   analyzing said set of respective parameters to determine a statistically significant brain disease profile which fits said patient based on the at least one feature of interest of the patient's brain scan image;
   extracting from the database an initial dataset containing a respective brain disease profile of a plurality of patients based on the at least one feature of interest;
   creating an enhanced dataset containing at least partial data in the initial dataset for which the corresponding parameters have been determined empirically to provide a better match to the brain disease profile; and
   using the enhanced dataset to determine the statistically significant brain disease profile which fits said patient based on the at least one feature of interest of the patient's brain scan image.

2. The method according to claim 1, further including updating the database with corresponding parameters associated with the at least one feature of interest of the patient's brain scan image.

3. The method according to claim 2, further including:
   standardizing the at least one brain scan image of the patient to a standard image size so as to form a standardized image;
   measuring one or more dimensions of features in the standardized image; and
   inputting said one or more dimensions of features in the standardized image into the database in respect of the feature of interest.

4. The method according to claim 3, wherein updating the database includes inputting the standardized image into the database in respect of the feature of interest.

5. The method according to claim 2, wherein updating the database includes autocropping, extracting and masking a specified plurality of features and regions and/or parameters within the at least one brain scan image.

6. The method according to claim 2. wherein updating the database includes:
   pinpointing at least one reference point in the at least one brain scan image;
   determining one or more respective parameters associated with each reference point; and
   inputting said one or more respective parameters into the database in association with the reference points in the respective feature of interest.

7. The method according to claim 6, wherein pinpointing at least one reference point in the at least one brain scan image includes matching at least one brain scan image against corresponding template images.

8. The method according to claim 7, including embedding known reference points within the at least one brain scan image.

9. The method according to claim 6, pinpointing at least one reference point in the at least one brain scan image includes setting the palm, hand or foot in an encompassing fixed shell before imaging thereby referencing from the outer shell.

10. The method according to claim 9, further comprising measuring one or more in the group containing: hardness and softness of skin and palm mounts, bending angle of the fingers and finger formations on closed or clapped hands.

11. The method according to claim 10, including pressing automatically on the skin and palm mounts.

12. The method according to claim 1, wherein the at least one feature of interest is a brain morphology or functionality.

13. The method according to claim 1, wherein the respective parameters include one or more in the group of: medical profiles, psychiatric profiles, psychological profiles, cerebral fluid content profiles, genetic profiles, morphological volume measurements of brain features, limb data, chemical analysis data, and data relating to CSF, gray matter, ventricular fluid, lesioned tissue white matter, neurological mapping of activity to specified stimuli such as specific sight, sound, vocal, smell, touch, taste, suggested imagination.

14. The method according to claim 1, wherein analyzing said set of respective parameters includes one or more in the group of: voting, matching, correlating the respective brain disease profile associated with the at least one searched feature.

15. The method according to claim 1, wherein creating the enhanced dataset includes augmenting the initial dataset by a respective brain disease profile of a plurality of patients based on at least one additional feature of interest.

16. The method according to claim 1, wherein creating the enhanced dataset includes reducing the initial dataset by rejecting a respective brain disease profile of a plurality of patients based on at least one rejected feature of interest.

17. The method according to claim 1, wherein the at least one brain scan image of a patient is obtained using an MRI scanner, fMRI, MRS, PET, or other.

18. The method according to claim 1, wherein the at least one brain scan image of a patient is provided in a form of a computer memory of 2-D slices forming a 3-D map or alternatively of a complete 3-D image.

19. The method according to claim 1, including extracting parameters by reference to known given or calculated reference points in the at least one brain scan image.

20. The method according to claim 1 used for evaluating psychiatric analysis of the patient.

21. The method according to claim 20, wherein the parameters relate to readings of hand and foot palms.

22. A method for automatic diagnosis of possible brain disease, said method comprising:
   obtaining at least one brain scan image of a patient containing at least one feature of interest and a corresponding result of a medical profile analysis of the patient;
   searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile;
   analyzing said set of respective parameters to determine a statistically significant brain disease profile which fits said patient based on the at least one feature of interest of the patient's brain scan image;
   said method further including:
   a) obtaining a 3-D brain scan image and the result of a psychiatric profile analysis and parameters used to enhance the image of the scan;
   b) extracting the edges of the brain scan image, pinpointing reference points on it, positioning, standardizing its size, and aligning it;
   c) autocropping, extracting and masking a specified plurality of features and regions and/or parameters within the brain scan;
   d) voting, matching or correlating extracted regions, images and parameters of a plurality of features of the scan with database template images and parameters;
   e) searching in a message memory for a plurality of messages that make up the profile of an individual, wherein each message corresponds to the respective feature or combination of features of a database, outputting each one of the said plurality of messages concurrently to form a first profile set of messages;
   f) obtaining a second set of feature detections and related message statements;
   g) accepting some output detections and related messages in the first set to form a third profile set of features and related messages that is a subset of the first set, combining the third profile set of messages with the second set to form a fourth set, alternatively allowing the fourth set to equal the first set, alternatively allowing the third set to equal the second set;
   h) storing in the said message memory the fourth set of detections and related messages corresponding to the said brain scan image or storing in the said message memory the fourth set of detections and related messages corresponding to a new combination of features on the brain scan image, providing a corrected output based on said corrected fourth set of detections and related messages.

23. The method according to claim 22, including extracting areas and features by reference to known given or calculated reference points.

24. A system for automatic diagnosis of possible brain disease, said system comprising:
   a data extraction unit for searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile; and
   an analysis unit coupled to the data extraction unit for analyzing said set of respective parameters to determine a statistically significant brain disease profile which fits said patient based on at least one feature of interest of a brain scan image of the patient;
   said data extraction unit being adapted to extract from the database an initial dataset containing a respective brain disease profile of a plurality of patients based on the at least one feature of interest and create an enhanced dataset containing at least partial data in the initial dataset for which the corresponding parameters have been determined empirically to provide a better match to the brain disease profile; and
   said an analysis unit being adapted to use the enhanced dataset to determine the statistically significant brain disease profile which fits said patient based on the at least one feature of interest of the patient's brain scan image.

25. The system according to claim 24, wherein the analysis unit comprises a neural network.

26. A computer readable medium, tangibly embodying a program of instructions executable by a computer to perform a method for automatic diagnosis of possible brain disease based on at least one brain scan image of a patient containing at least one feature of interest and a corresponding result of a medical profile analysis of the patient, said method comprising:

searching a database containing parameters associated with at least one feature of a plurality of brain scan images each compiled from respective patient data and inserted into the database so as to extract from the database a set of respective parameters each associated with said at least one feature and wherein in respect of each feature at least one of the corresponding parameters is indicative of a brain disease profile;

analyzing said set of respective parameters to determine a statistically significant brain disease profile which fits said patient based on the at least one feature of interest of the patient's brain scan image;

extracting from the database an initial dataset containing a respective brain disease profile of a plurality of patients based on the at least one feature of interest;

creating an enhanced dataset containing at least partial data in the initial dataset for which the corresponding parameters have been determined empirically to provide a better match to the brain disease profile; and using the enhanced dataset to determine the statistically significant brain disease profile which fits said patient based on the at least one feature of interest of the patient's brain scan image.

* * * * *